(12) United States Patent
Vergano et al.

(10) Patent No.: US 7,726,173 B2
(45) Date of Patent: Jun. 1, 2010

(54) HAMMER FOR A CHARPY PENDULUM

(75) Inventors: Stefano Vergano, Pianezza (IT); Flavio Cometti, Pianezza (IT)

(73) Assignee: CEAST S.p.A., Pianezza (Turin) (IT)

( * ) Notice: Subject to any disclaimer, the term of this patent is extended or adjusted under 35 U.S.C. 154(b) by 0 days.

(21) Appl. No.: 12/253,055

(22) Filed: Oct. 16, 2008

(65) Prior Publication Data
US 2009/0100904 A1    Apr. 23, 2009

(30) Foreign Application Priority Data
Oct. 17, 2007   (IT)  .......................... TO2007A0730

(51) Int. Cl.
*G01M 7/00* (2006.01)
(52) U.S. Cl. .................................... 73/12.14
(58) Field of Classification Search ................. 73/12.14
See application file for complete search history.

(56) References Cited

U.S. PATENT DOCUMENTS

| | | | | |
|---|---|---|---|---|
| 2,359,044 A | * | 9/1944 | MacBride | 73/844 |
| 2,757,694 A | * | 8/1956 | Curtis | 81/22 |
| 2,934,049 A | * | 4/1960 | Spurlin | 173/127 |
| 3,999,420 A | * | 12/1976 | Wright | 73/12.14 |
| 4,660,832 A | * | 4/1987 | Shomo | 16/431 |
| 7,051,390 B2 | * | 5/2006 | van Beek | 7/145 |
| 2007/0289760 A1 | * | 12/2007 | Sterling et al. | 173/104 |

* cited by examiner

*Primary Examiner*—Lisa M Caputo
*Assistant Examiner*—Octavia Davis
(74) *Attorney, Agent, or Firm*—Patterson & Sheridan, L.L.P.

(57) ABSTRACT

A hammer for a Charpy pendulum, comprising a body including a head and an arm, wherein the arm is equipped with a portion for attachment to an end opposite to that of the head and wherein the head has a general C-shape, with a concave part in which an area of impact is situated. The arm and the head of said body are obtained in a monolithic form by perimetral cutting of a plane plate.

19 Claims, 8 Drawing Sheets

HAMMER FOR A CHARPY PENDULUM

CROSS-REFERENCE TO RELATED APPLICATIONS

This application claims benefit of Italian patent application number TO2007A000730, filed Oct. 17, 2007, which is herein incorporated by reference.

BACKGROUND OF THE INVENTION

1. Field of the Invention

The present invention relates in general to equipment for impact tests on plastic materials. More precisely, the invention relates to a hammer for a Charpy pendulum. As is known, the Charpy pendulum is a measuring instrument that is basically made up of a supporting structure having a rotating shaft with horizontal axis, fixed to which is a hammer that has the purpose of striking a specimen with a preset energy. The hammer must be designed and built so as to approximate as accurately as possible the behaviour of an ideal pendulum having an equivalent mass concentrated in the point of impact with the specimen.

2. Description of the Related Art

In traditional solutions, the hammer comprises a metal block fixed to the end of a rod that constitutes the arm of the hammer. The traditional solutions derive from the need to position the centre of gravity of the hammer at the point of impact of the head. Traditionally, the arm of the hammer is formed by a relatively thin rod with a weight as small as possible with respect to the weight of the head.

The known solutions involve difficulties from the production standpoint, in particular since they require three different components (the head, the rod, and a device for fixing the rod to the shaft of the pendulum) that must be fixed to one another with high precision.

SUMMARY OF THE INVENTION

The object of the present invention is to provide a hammer for a Charpy pendulum that will be constructively simpler and will have a greater precision than hammers of a known type.

According to the present invention, said object is achieved by a hammer having a body including a head and an arm, wherein the arm is equipped with a portion for attachment to an end opposite to that of the head and wherein the head has a general C-shape, with a concave part in which an area of impact is situated. The arm and the head of the body are obtained in a monolithic form by perimetral cutting of a plane plate.

The hammer according to the present invention comprises a body including an arm and a head obtained in a monolithic form by means of perimetral cutting of a plane plate.

The solution according to the present invention enables facilitation of design of the hammer as compared to traditional solutions. The hammer according to the present invention is characterized by a high simplicity of fabrication and does not require operations of assembly between the arm and the head. The fact of making the arm and the head of the body of the hammer in a monolithic form moreover enables a greater precision to be obtained as compared to the solutions of a known type. The new shape of the hammer enables adoption of particularly simple solutions for the application of the weights and for attachment of the hammer to the shaft of the pendulum.

BRIEF DESCRIPTION OF THE DRAWINGS

Further characteristics and advantages of the present invention will emerge clearly from the ensuing detailed description, which is provided purely by way of non-limiting example, with reference to the attached drawings, wherein.

DETAILED DESCRIPTION

With reference to the drawings, designated by 10 is a hammer for a Charpy pendulum according to the present invention. The hammer 10 comprises a monolithic body 12, in which an arm 14 and a head 16 are defined.

According to the present invention, the body 12 is obtained in a monolithic form by means of perimetral cutting of a plane plate. The body 12 can be made of aluminium or alloys thereof, of steel or composite material. The perimetral cutting for formation of the body 12 can be obtained by means of any known technology, such as, for example, laser cutting, water cutting, milling, etc.

Since the body 12 is obtained starting from a plane plate, it has two parallel plane faces and has a uniform thickness. In particular, the arm 14 and the head 16 have the same thickness.

The body 12 has a shape substantially similar to that of a spanner. The head 16 has a general C-shape, with a concave part 18 open on one side of the head and closed on three sides. The bottom of the concave part 18 defines an area of impact, in which a percussion member 20 is applied. The percussion member 20 is, for example, made of steel and can be fixed to the head 16 by means of screws or the like.

The arm 14 is equipped with an attachment portion 22 located at the end of the arm 14 opposite to the head 16. The attachment portion 22 can have a thickness slightly smaller than the thickness of the arm 14.

Figure 1:
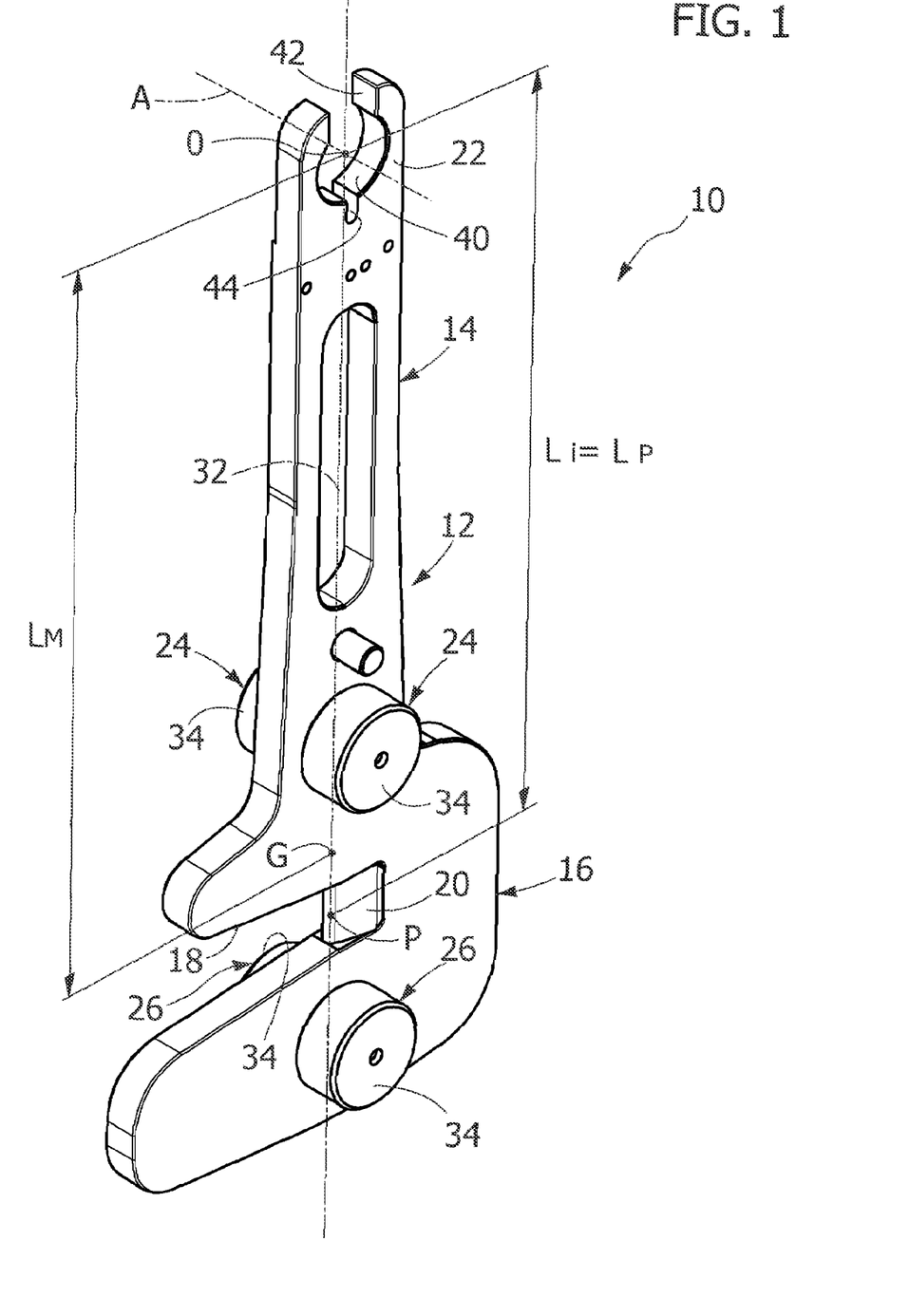
FIG. 1 is a perspective view of a hammer according to the present invention.

Designated by P in FIG. 1 is the point of impact with the specimen, and designated by O is the centre of rotation of the hammer 10. Moreover designated by A in FIG. 1 is the axis of rotation of the hammer 10. The axis A is a horizontal axis that passes through the centre of rotation O and is orthogonal to the main plane faces of the body 12.

The distance between the point of impact P and the centre of rotation O is designated by $L_i$. Denoted by $L_M$ is the distance of the centre of gravity G of the hammer 10 from the centre of rotation O.

Defined as $L_p$ is the reduced length of the arm of an ideal equivalent pendulum, i.e., a pendulum with a pointlike mass concentrated in a point located at the distance $L_p$ from the centre of rotation.

The reduced length of the equivalent ideal pendulum is given by the formula $$L_p = \frac{I_0}{M \cdot L_M}$$

The nominal energy of the hammer 10 $E_n$ is given by the formula $$E_n = M \cdot g \cdot L_M (1 - \cos \alpha_n)$$

where $I_0$ is the moment of inertia of the hammer 10 with respect to the axis of rotation A;

M is the overall mass of the hammer 10;

$L_M$ is the distance of the centre of gravity G of the hammer 10 from the axis of rotation A;

g is the acceleration of gravity; and $\alpha_n$ is the nominal (pre-set) angle of release of the pendulum.

The hammer 10 is designed and built in such a way that the length $L_i$ (FIG. 1) is equal to the reduced length $L_p$. The hammer 10 is moreover designed in such a way that the nominal energy $E_n$ is equal to a pre-set design value.

To obtain these conditions, the hammer 10 is provided with weights 24, 26, fixed on the opposite faces of the body 12. The weights 24, 26 are identical in opposed pairs so as to keep the centre of gravity of the hammer 10 centred on the axis 32.

Figure 2:
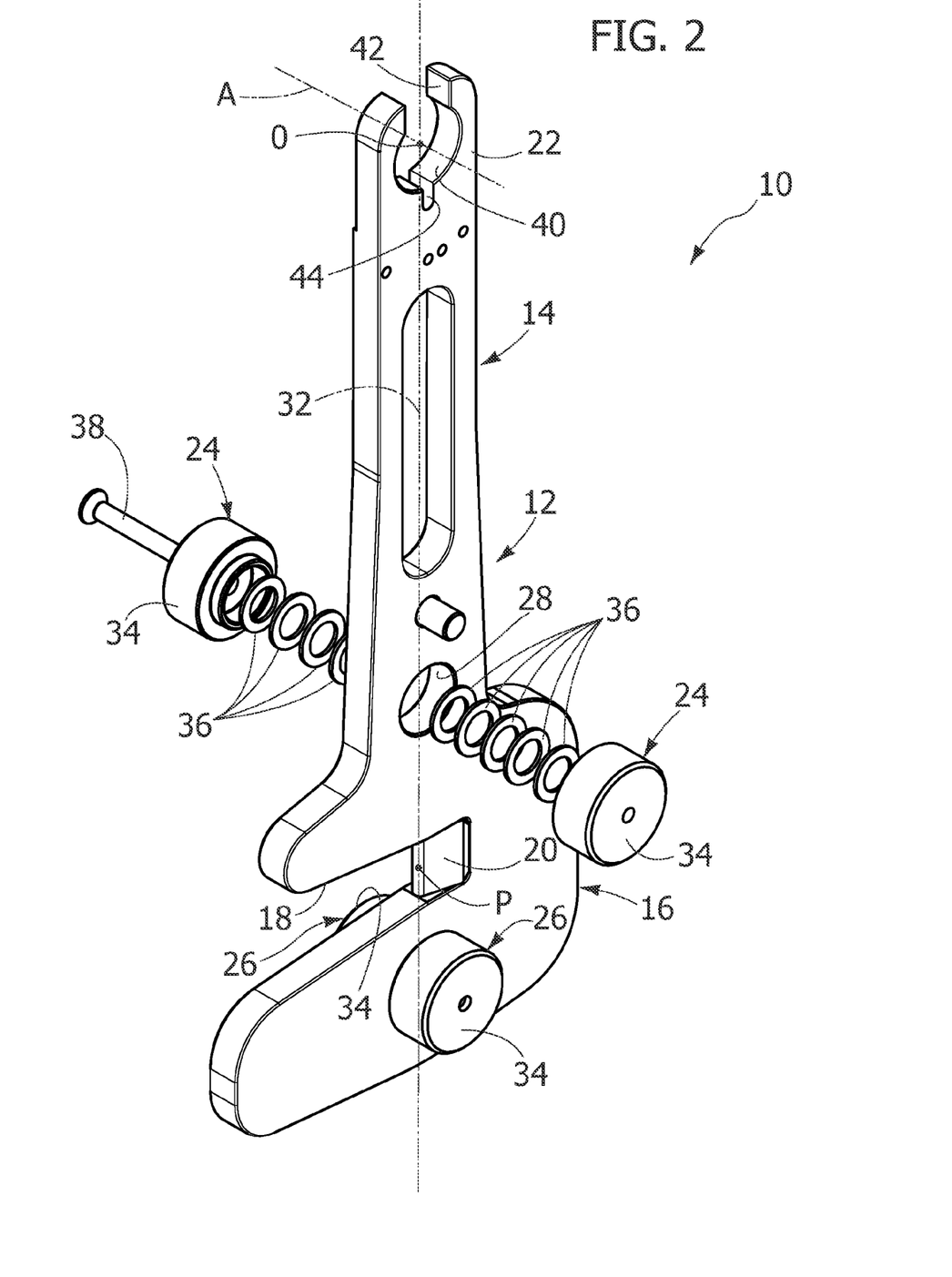
FIG. 2 is a partially exploded perspective view of the hammer of FIG. 1.
Figure 3:
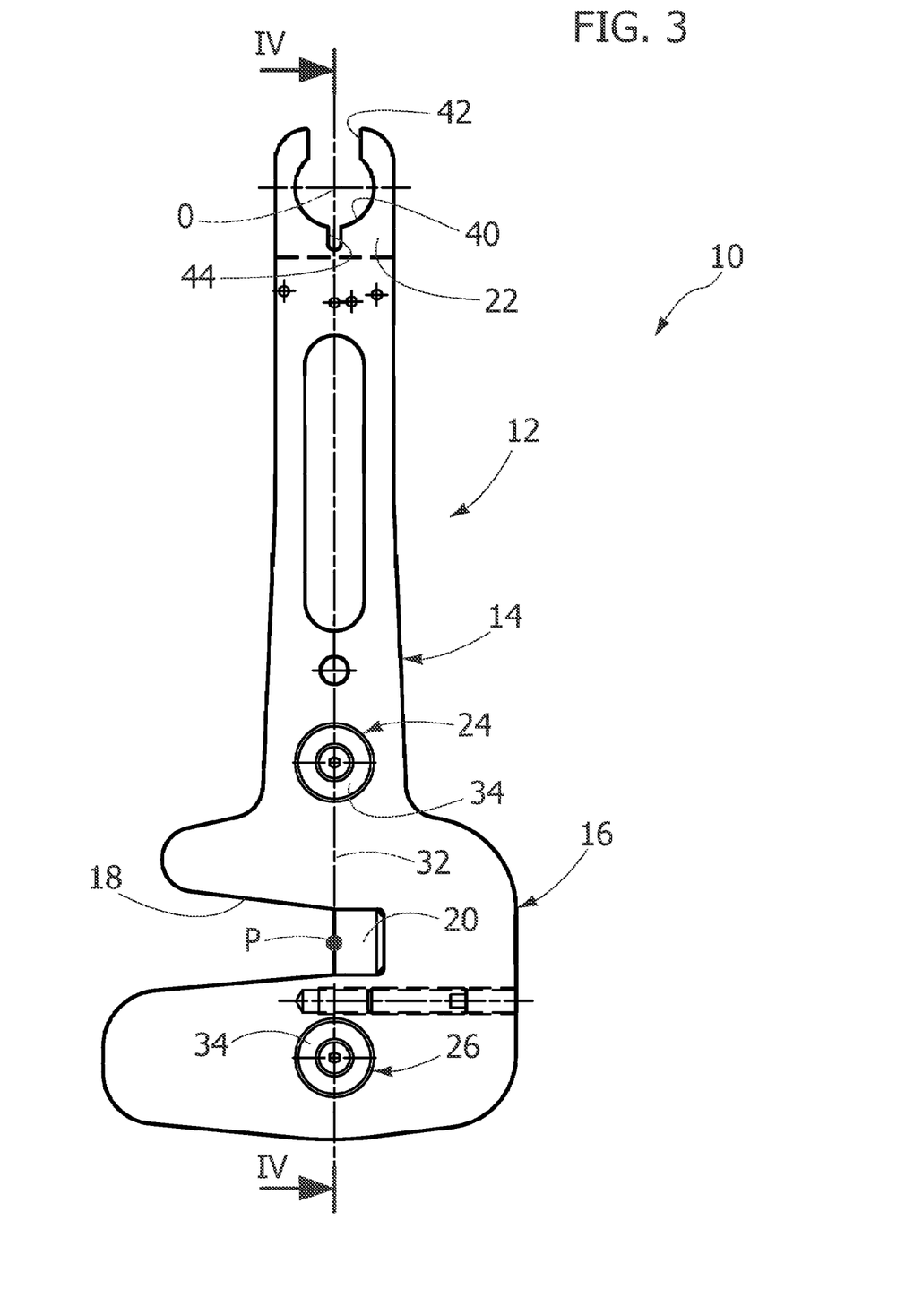
FIG. 3 is a front elevation of the hammer of FIG. 1.
Figure 4:
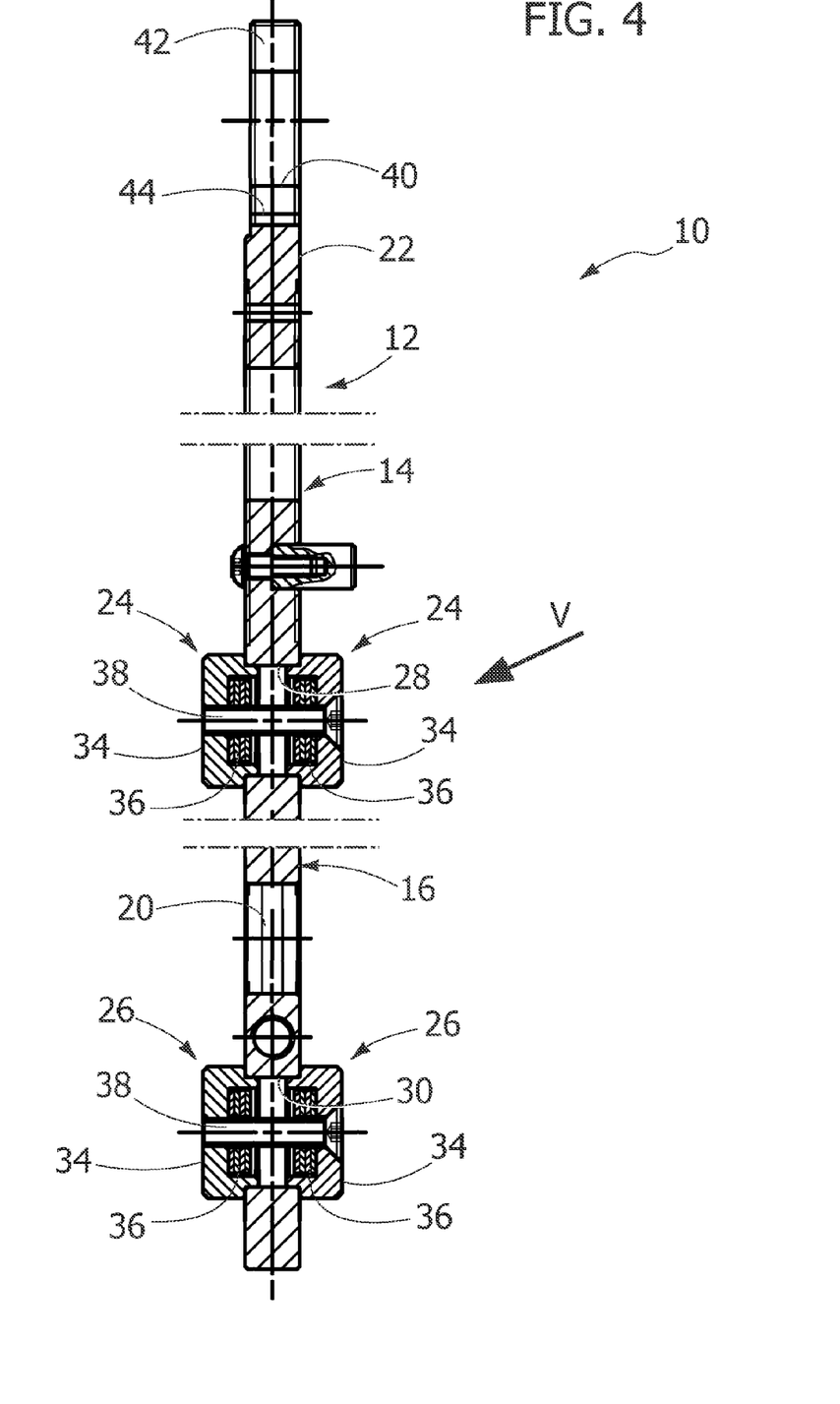
FIG. 4 is a cross section according to the line IV-IV of FIG. 3.
Figure 5:
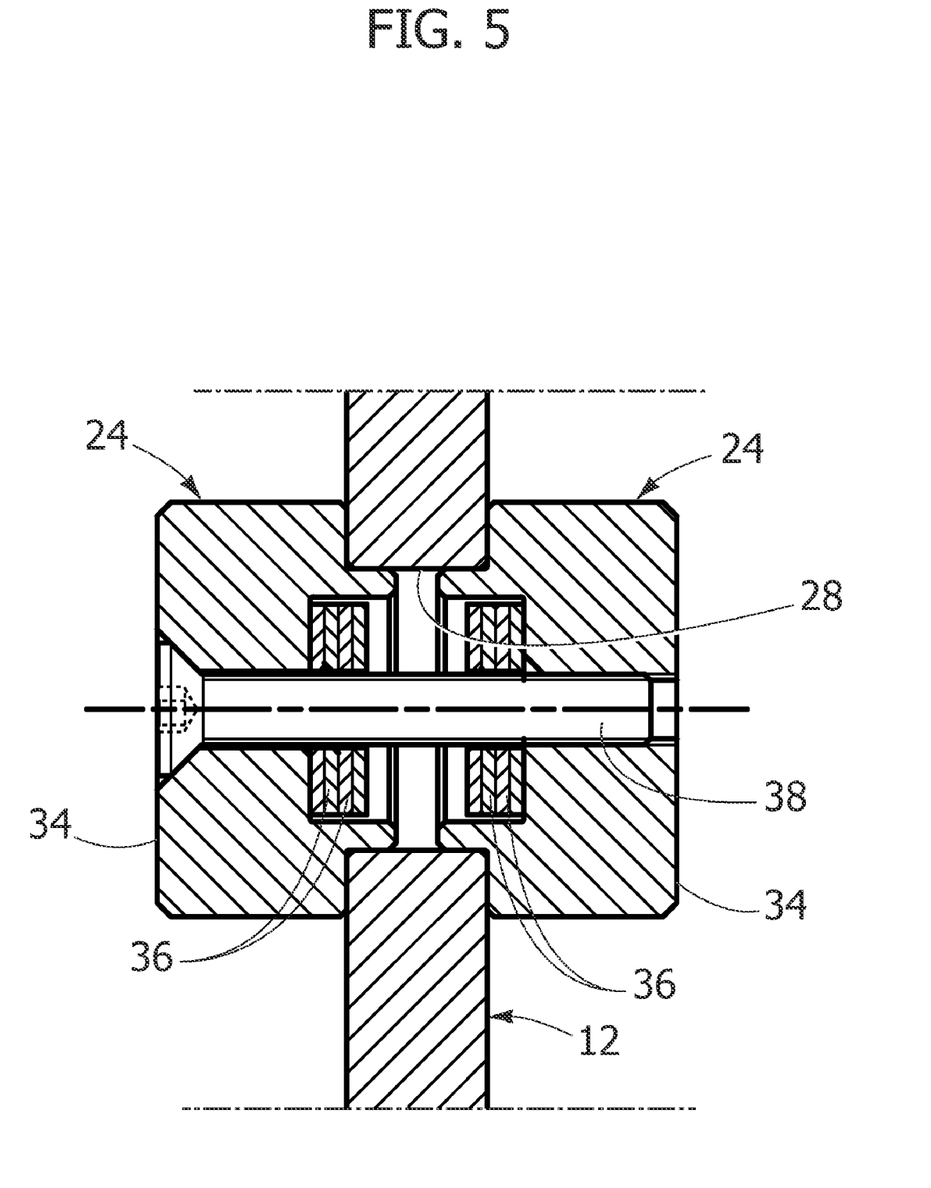
FIG. 5 is a cross section at a larger scale of the part indicated by the arrow V in FIG. 4.

With reference to FIGS. 2, 4 and 5, the body 12 is provided with through holes 28, 30 set in the areas of application of the weights 24, 26. The centres of the holes 28, 30 are located on an axis 32 that joins the point of impact P with the centre of rotation O. The weights 24, 26 are set on opposite sides with respect to the point of impact P. In particular, the weights 24 are arranged between the point of impact P and the centre of rotation O, and the weights 26 are arranged between the point of impact P and the end of the head 16 opposite to the attachment portion 22. Each weight 24, 26 comprises a cylindrical hollow casing 34, housed within which are a plurality of commercial metal washers 36. The casings 34 couple with the respective hole 28, 30 on the opposite faces of the body 12 and are fixed to one another by means of a screw 38. The washers 36 are glued within the respective casings 34.

The weights 24, 26 are connected to the body 12 in a removable way so that it is possible to replace the weights 24, 26 on the same hammer 10 with others having a different a mass. The position of the weights 24, 26 is determined so that, by varying in the same way the mass and the moment of inertia of both of the pairs of weights 24, 26, the reduced length $L_p$ remains unvaried. Consequently, it is possible to vary the nominal energy $E_n$ of the hammer 10 without varying the length of impact $L_i$.

It is also possible to vary the number of washers 36, maintaining the casings 34 unvaried. If the number of the washers is varied in the same way for both pairs of weights 24, 26, the nominal energy of the hammer can be calibrated with precision, maintaining the value of the reduced length $L_p$ unvaried. Alternatively, by varying in a differentiated way the number of the washers 36 in the two pairs of weights 24, 26, it is possible to regulate the reduced length $L_p$ precisely.

The flattened shape of the body 12 enables attachment of the hammer 10 to the rotating shaft of the pendulum in a particularly simple and effective way. According to a preferred embodiment of the present invention, the attachment portion 22 comprises a hole 40 orthogonal to the main faces of the body 12 and having an open edge 42. The width of the open edge 42 is smaller than the diameter of the hole 40. Preferably, the hole 40 communicates with a positioning notch 44.

Figure 6:
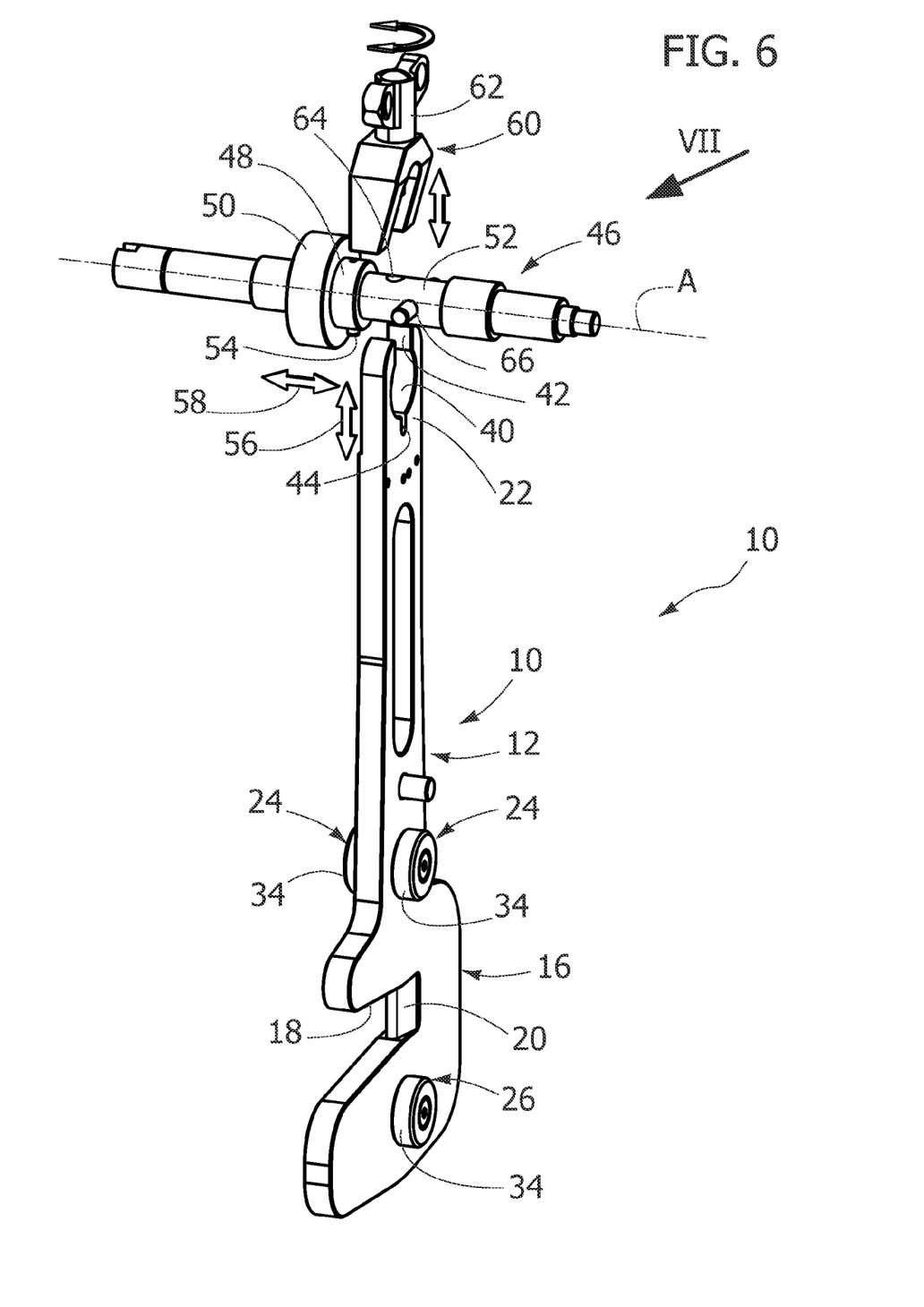
FIG. 6 is a perspective view illustrating assembly of the hammer according to the present invention on the shaft of a pendulum.

With reference to FIG. 6, designated by 46 is the rotating shaft of a Charpy pendulum. The shaft 46 is carried by the fixed structure of the pendulum (not illustrated) in such a way that it can turn freely about a horizontal axis A. The shaft 46 has an attachment portion 48 that is designed to couple with the portion 22 for attachment of the hammer 10. The attachment portion 48 of the shaft 46 has a cylindrical shape with a diameter substantially equal to the diameter of the hole 40 and a length slightly smaller than the thickness of the portion 22 for attachment of the hammer 10. Provided on one side of the attachment portion 48 is a shoulder 50 with a diameter larger than the diameter of the attachment portion 48. Provided on the opposite side of the attachment portion 48 is a portion of shaft 52 with a diameter smaller than the width of the open edge 42 of the hammer 10. The attachment portion 48 of the shaft 46 has a small projection 54 that is designed to couple with the positioning notch 44 provided in the portion 22 for attachment of the hammer 10.

Figure 7:
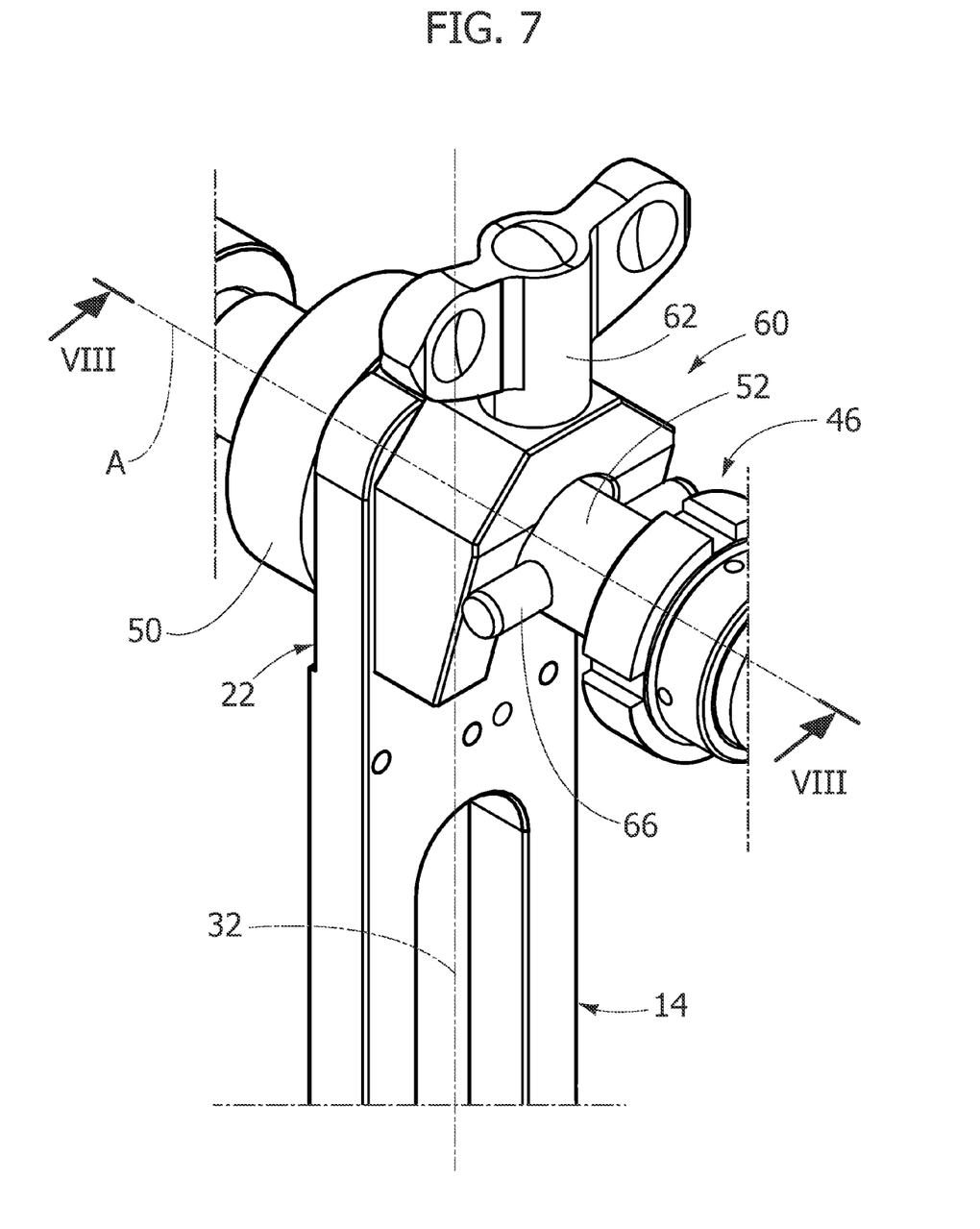
FIG. 7 is a perspective view at a larger scale of the part indicated by the arrow VII in FIG. 6.
Figure 8:
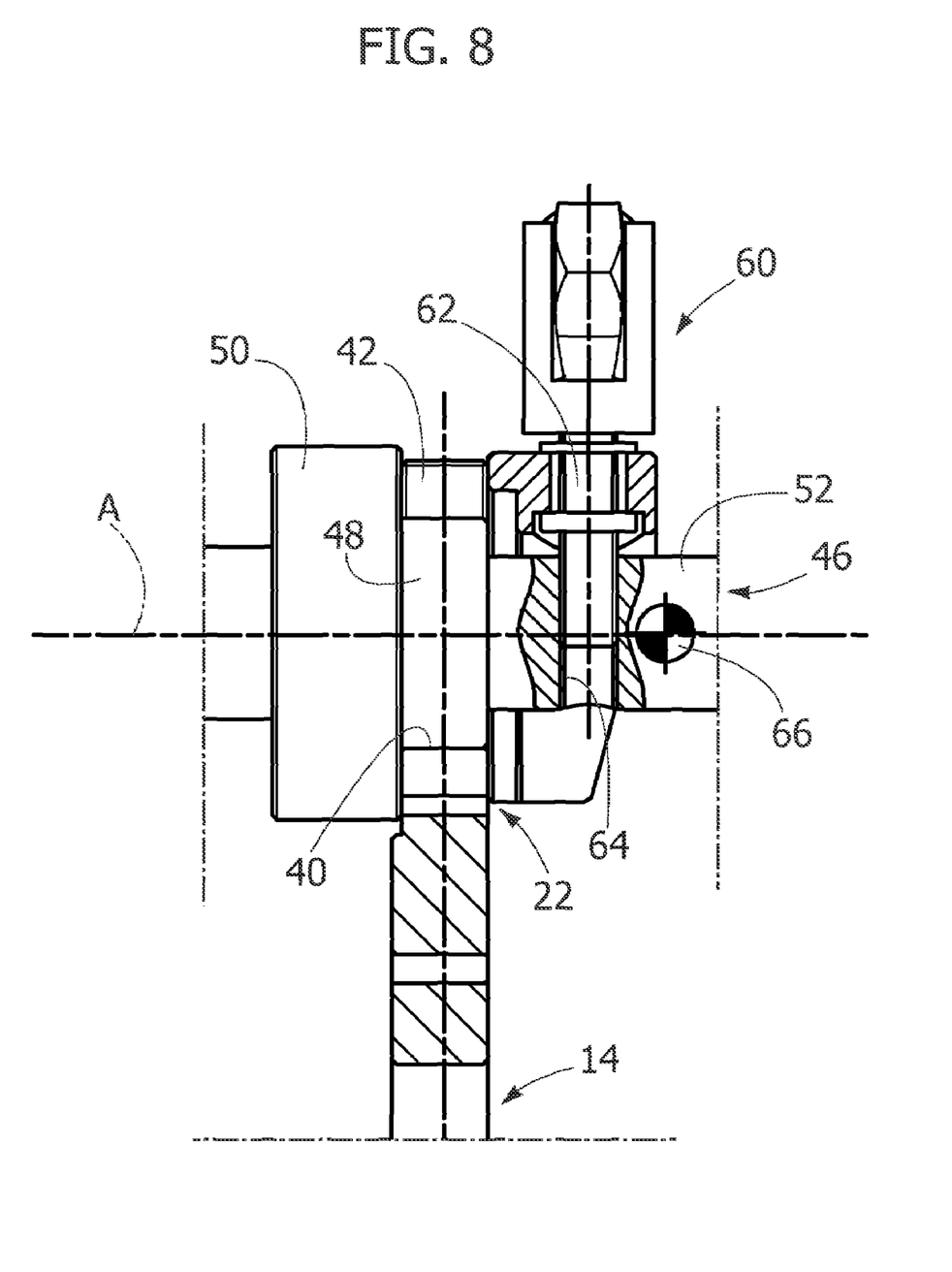
FIG. 8 is a partial cross section according to the arrow VIII-VIII of FIG. 7.

Assembly of the hammer 10 on the shaft 46 is performed by positioning initially the hole of the hammer 10 on the portion of shaft 52 with a small diameter in the direction indicated by the arrow 56 in FIG. 6. Then, the hammer 10 is displaced in an axial direction (in the direction indicated by the arrow 58) for coupling the hole 40 with the attachment portion 48. During this second movement, the hammer 10 is oriented so as to align the notch 44 with the projection 54 in order to obtain a pre-set angular positioning between the hammer 10 and the shaft 46. When the hole 40 of the hammer 10 is coupled with the attachment portion 48 of the shaft 46, the hammer 10 is supported by the shaft 46. Fixing of the hammer 10 is completed by means of a blocking member 60 that blocks the hammer 10 in an axial direction against the shoulder 50. With reference to FIGS. 6, 7 and 8, the blocking member 60 is a fork-shaped wedgelike element that is inserted on the portion with smaller diameter 52 of the shaft 46. The blocking member 60 has a wing screw 62 that engages a threaded hole 64 provided in the portion 52 of the shaft 46. Provided on the portion of shaft 52 is a transverse pin 66, against which the wedge-shaped part of the blocking member 60 acts. It will be appreciated that by screwing the screw 62 in the hole 64, the blocking member is inserted in a forced way between the transverse pin 66 and the plane surface of the portion 22 for attachment of the hammer 10, by axially compressing the attachment portion 22 against the shoulder 50 of the shaft 46. The fact that the hammer 10 is self-supported also prior to insertion of the blocking member 60 enables screwing of the screw 62 and fixing of the hammer 10 on the shaft 46 in a particularly simple and convenient way.

While the foregoing is directed to embodiments of the present invention, other and further embodiments of the invention may be devised without departing from the basic scope thereof, and the scope thereof is determined by the claims that follow.

The invention claimed is:

1. A hammer for a Charpy pendulum, the hammer comprising:

a body including a head and an arm, wherein the arm is equipped with a portion for attachment to an end opposite to that of the head and wherein the head has a general C-shape, with a concave part situated in which is an area of impact, wherein the arm and the head of said body are obtained in a monolithic form by means of perimetral cutting of a plane plate and;

a percussion member connected to the concave part of the head by at least one attachment member.

2. The hammer according to claim 1, wherein the percussion member is applied in said area of impact.

3. The hammer according to claim 1, further comprising a plurality of weights applied on opposite faces of the body.

4. The hammer according to claim 3, further comprising a first pair of weights and a second pair of weights, wherein the weights have a mass and dimensions substantially equal to one another.

5. The hammer according to claim 4, wherein the weights are positioned on the body so that by varying the mass and the moment of inertia of the weights in a way equal to one another it is possible to vary the nominal energy of the hammer maintaining the reduced length of the hammer unaltered.

6. The hammer according to claim 3, wherein the weights can be varied in pairs to calibrate the reduced length and the nominal energy of the hammer.

7. The hammer according to claim 3 wherein each of said weights comprises a plurality of washers disposed in a hollow casing.

8. The hammer according to claim 1, wherein said attachment section comprises a through hole with an open edge having a width smaller than the diameter of the hole.

9. The hammer according to claim 8, further comprising a wedge-shaped blocking member designed to block said attachment portion axially.

10. The hammer according to claim 1, further comprising a first pair of weights and a second pair of weights set on the body at opposite sides with respect to the area of impact.

11. The hammer according to claim 10, wherein the said first pair of weights are positioned on the body between the area of impact and an end of the head.

12. The hammer according to claim 11, wherein the said second pair of weights are positioned on the body between the area of impact and a centre of rotation of the hammer.

13. The hammer according to claim 10, wherein the arm and the head have the same thickness.

14. A hammer configured to be mounted on a shaft of a Charpy pendulum, the hammer comprising:
  a body having a head portion, an arm portion and an attachment portion, wherein the head includes a concave part that defines an area of impact and wherein the attachment portion is configured to mate with a portion of the shaft and the attachment portion includes a through hole with an open edge having a width smaller than the diameter of the hole; and
  a first pair of weights positioned on the body on one side of the area of impact and a second pair of weights positioned on the body on another side of the area of impact.

15. The hammer according to claim 14, further comprising a percussion member attached to the concave part of the head proximate the area of impact.

16. The hammer according to claim 14, wherein the head portion and the arm portion have the same thickness.

17. The hammer according to claim 14, wherein the first pair of weights are located on the head portion.

18. The hammer according to claim 14, wherein the attachment portion includes a positioning notch that is configured to mate with a projection on the shaft.

19. The hammer according to claim 14, wherein the arm and the head of said body are obtained in a monolithic form by perimetral cutting of a plane plate.

* * * * *